(12) United States Patent
Benco

(10) Patent No.: US 11,255,810 B2
(45) Date of Patent: Feb. 22, 2022

(54) ADHESIVE-POLYMER CONTAINING MEMBRANES FOR IN VITRO DIAGNOSTIC DEVICES

(71) Applicant: Siemens Healthcare Diagnostics Inc., Tarrytown, NY (US)

(72) Inventor: John Benco, Holliston, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 148 days.

(21) Appl. No.: 16/645,937

(22) PCT Filed: Sep. 13, 2018

(86) PCT No.: PCT/US2018/050834
§ 371 (c)(1),
(2) Date: Mar. 10, 2020

(87) PCT Pub. No.: WO2019/055622
PCT Pub. Date: Mar. 21, 2019

(65) Prior Publication Data
US 2020/0200698 A1 Jun. 25, 2020

Related U.S. Application Data

(60) Provisional application No. 62/558,543, filed on Sep. 14, 2017.

(51) Int. Cl.
*G01N 27/327* (2006.01)
*G01N 27/333* (2006.01)
*G01N 33/543* (2006.01)

(52) U.S. Cl.
CPC ..... *G01N 27/3275* (2013.01); *G01N 27/3271* (2013.01); *G01N 27/3335* (2013.01); *G01N 33/54353* (2013.01)

(58) Field of Classification Search
None
See application file for complete search history.

(56) References Cited

U.S. PATENT DOCUMENTS

| 7,622,533 B2 | 11/2009 | Lee |
| 7,927,620 B2 | 4/2011 | Benco |
| (Continued) | | |

FOREIGN PATENT DOCUMENTS

| WO | 2015155665 A1 | 10/2015 |
| WO | 2016105503 A1 | 6/2016 |
| WO | 2017068425 A1 | 4/2017 |

OTHER PUBLICATIONS

International Search Report and Written Opinion of International Application No. PCT/US2018/050834 dated Nov. 14, 2018.
(Continued)

*Primary Examiner* — J. Christopher Ball
(74) *Attorney, Agent, or Firm* — Dunlap Codding, P.C.

(57) ABSTRACT

In vitro diagnostic sensors are disclosed that include membranes formed of a polymer matrix that has been modified to contain surface adhesion functional group(s) that enables attachment of the membrane to a substrate of the sensor. Also disclosed are membranes of these sensors as well as multi-sensor arrays that include multiple sensors. In addition, methods of producing and using these membranes, sensors, and arrays are disclosed.

20 Claims, 4 Drawing Sheets

(56) References Cited

U.S. PATENT DOCUMENTS

| | | | |
|---|---|---|---|
| 2006/0091009 A1* | 5/2006 | Harman, III | G01N 27/4035 204/416 |
| 2008/0171836 A1* | 7/2008 | Lee | C08G 71/04 525/418 |
| 2009/0018642 A1 | 1/2009 | Benco | |
| 2009/0275066 A1 | 11/2009 | Popot et al. | |
| 2011/0105712 A1 | 5/2011 | Jiang et al. | |
| 2011/0286888 A1 | 11/2011 | Barlag | |
| 2015/0082874 A1 | 3/2015 | Samproni et al. | |
| 2017/0224876 A1 | 8/2017 | Babcock et al. | |

OTHER PUBLICATIONS

European Search Report and Written Opinion of European Application No. 18855392.9 dated Nov. 12, 2020.

Ryou et al., "Mussel-Inspired Adhesive Binders for High-Performance Silicon Nanoparticle Anodes in Lithium-Ion Batteries", Mar. 20, 2013, Advanced Materials, vol. 25, No. 11, pp. 1571-1576.

Pawlak et al., "Chemical Modification of Polymer Ion-Selective Membrane Electrode Surfaces", Jan. 23, 2014, Electroanalysis, vol. 26, No. 6, pp. 1121-1131.

Moulay, Saad, "Dopa/Catechol-Tethered Polymers: Bioadhesives and Biomimetic Adhesive Materials", May 5, 2014, Polymer Reviews, vol. 54, Issue 3, pp. 436-513.

Dalsin et al., "Protein Resistance of Titanium Oxide Surfaces Modified by Biologically Inspired mPEG-DOPA", 2005, Langmuir, vol. 21, No. 2, pp. 640-646.

Forooshani et al., "Recent Approaches in Designing Bioadhesive Materials Inspired by Mussel Adhesive Protein", published online Oct. 11, 2016, Journal of Polymer Science, Part A: Polymer Chemistry, vol. 55, pp. 9-33.

Lee et al., "Single-Molecule Mechanics of Mussel Adhesion", Aug. 29, 2006, Proceedings of the National Academy of Sciences of the United States of America, vol. 103, No. 35, pp. 12999-13003.

* cited by examiner

ADHESIVE-POLYMER CONTAINING MEMBRANES FOR IN VITRO DIAGNOSTIC DEVICES

CROSS REFERENCE TO RELATED APPLICATIONS/INCORPORATION BY REFERENCE STATEMENT

The subject application claims benefit under 35 USC § 119(e) of U.S. provisional Application No. 62/558,543, filed Sep. 14, 2017. The entire contents of the above-referenced patent application are hereby expressly incorporated herein by reference.

STATEMENT REGARDING FEDERALLY SPONSORED RESEARCH OR DEVELOPMENT

Not Applicable.

BACKGROUND

A sensor, also called a detector, is a device that measures a physical quantity and converts it to a signal which may be read by an observer or by an instrument. Sensors are used in chemical and biochemical testing to determine characteristics of an analyte of interest within a specimen or sample.

Sensor arrays, in which multiple sensors are grouped into a single unit, are useful in chemistry and medicine to determine the presence and/or concentration of multiple target analytes. For example, various types of analytical tests related to patient diagnosis and therapy can be performed by analysis of a liquid sample taken from a patient. Bodily fluids commonly tested include urine, blood, plasma, saliva, cerebrospinal fluid, pleural fluid, and the like. Blood samples, for example, are routinely analyzed to obtain measurements of the partial pressures of $CO_2$ and $O_2$ and concentrations of electrolytes and metabolites in the blood. Specifically, potentiometric sensors are often employed which can utilize an ion-selective electrode or an electrode having an ion-permeable membrane that selectively permits the ion of interest to diffuse through. The operating principle is based on the measureable potential difference that is created when an ion equilibrates between two phases.

In vitro diagnostic sensors are typically housed within clinical diagnostic instruments for simultaneous analysis of a large number of analytes. Currently, single-use sensors and multi-use sensors are available for use in sensor arrays, such as the sensor arrays set forth in U.S. Publication Nos. 2015/0082874 and 2011/0286888 and International Publication No. WO 2015/155665 (the entire contents of each of which are hereby expressly incorporated herein by reference).

Sensors which detect analytes having a biological component, such as cells, protein, or nucleic acid, are referred to as biosensors. One example of target analyte assays amenable to biosensor measurement include the use of enzymes that can detect the target analyte. In general, an enzyme is deposited on an electrode and "held in place" by cross-linking into an insoluble form for entrapment in a polymer. A cover membrane is then typically applied to further retain the enzyme and provide protection from fouling, interferents, etc. Particular (but non-limiting) examples of target analytes detectable by this type of biosensor include blood urea nitrogen (BUN), glucose, glutamate, lactate, ethanol, ascorbic acid, choline acetylcholine, creatinine, cholesterol, pyruvate, bilirubin, and the like.

Another example of in vitro diagnostic sensors currently in use is the ion selective electrode (ISE). ISEs are used to determine the presence and quantity of various ion analytes in biological samples and have become useful diagnostic techniques. Indeed, ISEs have been used to detect ion analytes such as (but not limited to) magnesium, sodium, potassium, calcium, chloride, and the like.

A number of different analyzers currently exist for making such measurements utilizing rigid layered sensor assemblies and electrical circuits. Such sensor assemblies are used to assess the condition of medical patients through primary clinical indications. Because of the frequency with which many patients are tested, the ability to use small sample sizes for performing analysis is desirable. Patients in intensive care units may require a sampling frequency of 15-20 per day for blood gas and clinical chemistry measurements. In these cases, analyzing small sample volumes is desirable, due to the relatively large number of samples taken in a relatively short period of time. Further, to limit the number of tests performed, it is desirable to gather as much information as possible with each test.

In particular, at the Point-of-Care (POC), there is a need for in vitro diagnostic (IVD) platforms that provide clinical results by using the smallest sample volume as possible. Typical currently available IVD systems require a minimum sample volume of 100 µL of whole blood to complete a full analysis. In some settings, 100 µL is too large of a sample, particularly in the neonatal intensive care unit (NICU). This has driven the need to reduce the size of the technologies used to make the measurements in IVD platforms and to create different types of substrates on which chemistries are applied.

Methods of producing in vitro diagnostic sensors are well known in the art, and these methods typically utilize chemistries that apply a sensing membrane to a surface of a substrate (such as, but not limited to, ceramic or glass). A gasket can be used to hold the membranes in place while being housed in various types of modules and arrays. In order to reduce complexity and sample size, new module designs have been created that do not utilize a gasket. These sensor production technologies typically utilize various additional layers of other materials that must be applied to the substrates to help improve adhesion; the mechanism of adhesion utilized in these is passive (i.e., electrostatic).

It has been shown that the catecholic amino acid 3,4-dihydroxyphenylalanine (DOPA) is the primary functional group in Mussel foot proteins (Mfps) and is responsible for the adhesive capability of the mollusk mussel (Dalsin et al., Langmuir, (2005) 21:640-646; and Forooshani et al., J. Polym. Sci., Part A: Polym. Chem. (2017) 55:9-33; the entire contents of each of which are expressly incorporated herein by reference); as disclosed therein, modified polymers containing the catecholic functional group (1,2-dihydroxybenzene), for example DOPA, or alternatively dopamine (3,4-dihydroxyphenethylamine), have been synthesized for new adhesives or glues that exhibit strong adhesion to a range of surfaces, including under long term exposure to aqueous environments. DOPA has been used to create surface-binding cell adhesion polypeptides and antifouling adhesive copolymers for cardiovascular stents (US Patent Application Publication No. 2009/0018642 and U.S. Pat. No. 7,927,620; the entire contents of which are incorporated herein by reference). In addition, DOPA modified linear polymers are disclosed in U.S. Pat. No. 7,622,533 (the entire contents of which are incorporated herein by reference).

DETAILED DESCRIPTION

Figure 1:
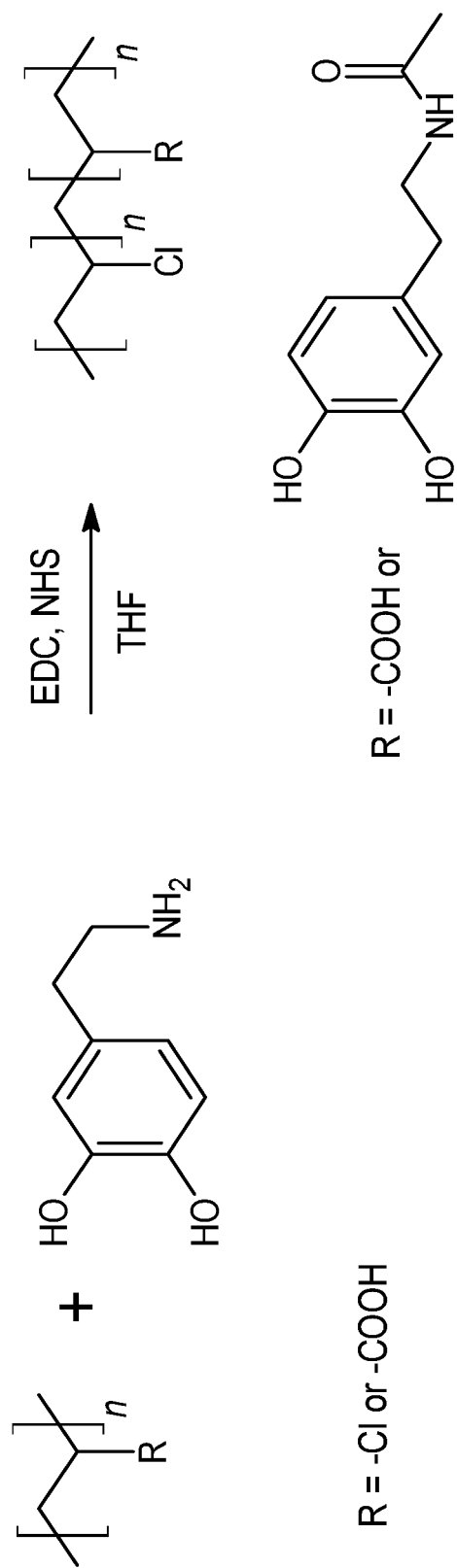
FIG. 1 schematically depicts the production of one non-limiting embodiment of a modified polymer comprising surface adhesion functional groups for use in production of membranes of in vitro diagnostic sensors in accordance with the presently disclosed inventive concept(s). EDC, N-(3-Dimethylaminopropyl)-N'-ethylcarbodiimide hydrochloride. NHS, N-hydroxy-succinimide. THF, Tetrahydrofuran.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, and/or methods disclosed herein can be made and executed without undue experimentation in light of the present disclosure. While the articles, compositions, and methods of the inventive concept(s) have been described in terms of particular embodiments, it will be apparent to those of skill in the art that variations may be applied to the articles, compositions and/or methods and in the steps or in the sequence of steps of the methods described herein without departing from the concept, spirit, and scope of the inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The term "sample" as used herein will be understood to include any type of biological sample that may be utilized in accordance with the presently disclosed inventive concept(s). Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "electrode" as used herein refers to any type of conductor or medium that is capable of functioning in accordance with the presently disclosed inventive concept(s). Non-limiting examples of electrodes that fall within the scope of the presently disclosed inventive concept(s) include electrochemical cells comprising a plurality of electrodes. Exemplary electrochemical cell constructs include a two-electrode cell comprising one indicator electrode and one reference electrode, a two-electrode cell comprising one anode and one cathode, a three-electrode cell comprising one anode, one cathode and one reference electrode, and a four-electrode cell comprising two working electrodes, one counter electrode, and one reference electrode.

In vitro diagnostic sensors are well known in the art, and typically utilize chemistries that apply a sensing membrane to a surface of a substrate. A gasket can be used to hold the created membranes in place while being housed in various types of modules and arrays. In order to reduce complexity and sample size, new module designs have been created that do not utilize a gasket. Therefore, the membranes must adhere to the substrate surface on their own accord and maintain adhesion under daily exposure to aqueous fluids at elevated temperatures (i.e., 37° C.) for several weeks. The membranes for ion selective electrodes (ISE's), used to measure for example magnesium, potassium, or sodium cations in blood, are typically made of 30% polyvinyl chloride (PVC) and a plasticizer, and these ISE membranes do not inherently stick to desirable substrates (such as, but not limited to, ceramic or glass). To combat this, these sensor production technologies typically utilize various additional layers of other materials that must be applied to the substrates to help improve adhesion; however, this is an added production step that can be quite costly. In addition, the mechanism of adhesion utilized in these methods is passive (i.e., electrostatic), and the level of long term adhesion under these conditions is unknown. Therefore, there is a need in the art for new and improved methods of producing in vitro diagnostic sensors comprising membranes with increased adhesion properties that allow for direct adhesion of the membrane to the substrate of the sensor. It is to such membranes having increased adhesion properties, as well as in vitro diagnostic sensors containing same, and methods of production and use thereof, that the presently disclosed inventive concept(s) is directed.

Certain non-limiting embodiments of the presently disclosed inventive concept(s) are directed to a membrane for an in vitro diagnostic sensor for detecting the presence and/or concentration of a target analyte in a fluidic biological sample. The membrane includes a polymer matrix comprising a polymer that has been modified to contain at least one surface adhesion functional group. The at least one surface adhesion functional group enables attachment of the membrane to a substrate of the in vitro diagnostic sensor.

Any polymer known in the art or otherwise contemplated herein that is capable of being formed into a membrane for an in vitro diagnostic sensor and that can function in accordance with the presently disclosed inventive concept(s) falls within the scope of the presently disclosed inventive concept(s). For example, but not by way of limitation, the polymer may be polyvinyl chloride, carboxylated-polyvinyl chloride, aminated-polyvinyl chloride, polyurethane, silicone, combinations thereof, and the like.

Any surface adhesion functional group known in the art or otherwise contemplated herein that is capable of modifying a polymer and subsequent incorporation into a membrane for an in vitro diagnostic sensor and that can function in accordance with the presently disclosed inventive concept(s) falls within the scope of the presently disclosed inventive concept(s). For example, but not by way of limitation, the surface adhesion functional group may comprise 3,4-dihydroxyphenylalanine (DOPA) and/or dopamine.

The surface adhesion functional group may be present on the polymer at any level that bestows adhesive properties to the modified polymer and thus to the membrane produced therefrom such that the membrane can function in accordance with the presently disclosed inventive concept(s).

The surface adhesion functional group may be present on the membrane at any percentage of concentration/surface area that allows the membrane to perform in accordance with the presently disclosed inventive concept(s). For example (but not by way of limitation), the surface adhesion functional group must be present on a sufficient amount of surface area of the membrane to allow for sufficient adhesion of the membrane to the substrate and maintain adhesion under daily exposure to aqueous fluids at testing temperatures for several weeks. In certain particular (but non-limiting) embodiments, the surface adhesion functional group may be present on the membrane surface at a percent concentration or percent surface area, or may be present at a weight percentage of the membrane, of about 0.01%, about 0.05%, about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 99%. In addition, the scope of the presently disclosed inventive concept(s) also includes the presence of the surface adhesion functional group on the membrane at any percent concentration or percent surface area, as well as the presence of the surface adhesion functional group at any weight percentage of the membrane, that falls within any range formed from the combination of two values listed above (for example, a range of from about 1% to about 99%, a range of from about 2% to about 80%, a range of from about 3% to about 60%, a range of from about 10% to about 95%, a range of from about 40% to about 75%, etc.).

In certain embodiments, the incorporation of the surface adhesion functional group into the polymer may create a modified polymer that is also so-called self-plasticized. In this case, the need for the addition of a separate plasticizer may be eliminated; this will reduce the complexity of the membrane formulation further as well as reduce steps in manufacturing and reduce costs while also increasing capacity.

Alternatively, the membrane may further comprise a plasticizer. Any plasticizer known in the art or otherwise contemplated herein and capable of functioning as part of the membranes described herein may be utilized in accordance with the presently disclosed inventive concept(s). Non-limiting examples of plasticizers that may be utilized include 2-Nitrophenyl octyl ether and [12-(4-Ethylphenyl) dodecyl] 2-nitrophenyl ether.

The membranes described herein may be utilized with any in vitro diagnostic sensors containing membranes applied to substrates that are known in the art or otherwise contemplated herein, where increasing adhesion of the membrane to the substrate is desirable. For example (but not by way of limitation), the membrane can be an ion-sensing membrane, such as (but not limited to), a cation sensing membrane (e.g., a magnesium sensing membrane, a calcium sensing membrane, a sodium sensing membrane, or a potassium sensing membrane) or an anion sensing membrane (e.g., a chloride sensing membrane). Alternatively, the membrane can be part of a biosensor. The membrane can be impermeable, semipermeable, or permeable.

The membrane may possess any shape that allows the sensor formed therefrom to function in accordance with the presently disclosed inventive concept(s). In addition, the membrane can be fabricated by any method known in the art or otherwise contemplated herein. Non-limiting examples of fabrication methods that can be utilized in accordance with the presently disclosed inventive concept(s) include screen printing, metal sputtering, photolithography, or any other standard membrane manufacturing method.

Certain non-limiting embodiments of the presently disclosed inventive concept(s) are directed to an in vitro diagnostic sensor for detecting the presence and/or concentration of a target analyte in a fluidic biological sample. The target analyte(s) detected by the in vitro diagnostic sensor may be any analyte present in a fluidic biological sample and that is known in the art or otherwise contemplated herein as being detectable by an in vitro diagnostic sensor. The in vitro diagnostic sensor comprises a substrate and any of the membranes described herein above or otherwise contemplated herein. The surface adhesion functional group present on the membrane attaches the membrane to the substrate.

Any type of substrate known in the art as capable of use with a membrane in an in vitro diagnostic sensor and to which the surface adhesion functional group can adhere can be utilized in accordance with the presently disclosed inventive concept(s). For example (but not by way of limitation), the substrate may be a potentiometric, amperometric, impedimetric, or conductometric sensor. In addition, any electrodes known in the art as capable of use with one of the above types of sensors can be utilized as the substrate in accordance with the presently disclosed inventive concept(s). Non-limiting examples of electrodes that may be utilized include ion-specific or ion-selective electrodes (ISE). The specific type of electrode selected will be dependent on the sensor type (i.e., potentiometric, amperometric, impedimetric, conductometric, etc.). In certain non-limiting embodiments, the electrode may contain a sensing layer. Any sensing layers that may be utilized with an electrode and that are known in the art or otherwise contemplatable by a person of ordinary skill in the art may be utilized in accordance with the presently disclosed inventive concept(s).

The surface adhesion functional group may directly interact with the surface of the substrate to attach the membrane to the substrate. Alternatively, the surface of the substrate may be provided with one or more functional groups that interact with the surface adhesion functional group to further increase the adhesion of the membrane to the substrate. For example (but not by way of limitation), DOPA-containing compounds are known to react with nucleophilic functional groups such as (but not limited to) primary amines (Lee et al., *Proc. Natl. Acad. Sci. USA*, (2006) 103:12999-13003; the entire contents of which are hereby expressly incorporated herein by reference).

Therefore, in certain non-limiting embodiments of the presently disclosed inventive concept(s), the substrate of the in vitro diagnostic sensor has at least one suitable functional group disposed on at least a portion of a surface thereof. In this embodiment, the surface adhesion functional group on the membrane interacts with the at least one suitable functional group disposed on the surface of the substrate to attach the membrane to the substrate. The suitable functional group may be any group that can attach to the surface of a substrate and interact with the surface adhesion functional group of the membrane to further increase the adhesion of the membrane to the substrate. In certain non-limiting embodiments, the suitable functional group is a nucleophilic functional group such as (but not limited to) nitrogen. A non-limiting example thereof is 3-Aminopropyl trimethoxysilane.

When present, the suitable functional group may be present on the surface of the substrate at any percentage of concentration/surface area that allows the membrane to attach firmly thereto. For example (but not by way of limitation), the suitable functional group must be present on a sufficient amount of surface area of the substrate to allow for sufficient adhesion of the membrane to the substrate and maintain adhesion under daily exposure to aqueous fluids at testing temperatures for several weeks. In certain particular (but non-limiting) embodiments, the suitable functional group may be present on the surface of the substrate at a percent concentration or percent surface area of about 0.01%, about 0.05%, about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 99%. In addition, the scope of the presently disclosed inventive concept(s) also includes the presence of the suitable functional group on the substrate at any percent concentration or percent surface area that falls within any range formed from the combination of two values listed above (for example, a range of from about 1% to about 99%, a range of from about 2% to about 80%, a range of from about 3% to about 60%, a range of from about 10% to about 95%, a range of from about 40% to about 75%, etc.).

The attachment of the surface adhesion functional group to the substrate, as well as the attachment of the surface adhesion functional group to the suitable functional group that may be disposed on the substrate, may occur by any type of mechanism, and thus the attachment of membrane to substrate is not limited to a particular type of interaction. For example (but not by way of limitation), Forooshani et al. (incorporated supra) discloses that DOPA can bind to both organic and inorganic surfaces through the formation of both covalent and non-covalent interactions, including, but not limited to, hydrogen bonds, $\pi$-$\pi$ electron interactions, cation-$\pi$ interactions, ionic crosslinking, coordination bonds, and the like. Therefore, the disclosure of any particular type of interaction herein, or illustration of any particular type of interaction in the Figures, is strictly for the purposes of illustration only and is not intended to be limiting of the scope of the presently disclosed inventive concept(s).

Any in vitro diagnostic sensors comprising membranes and substrates may be formed as described or otherwise contemplated herein. For example (but not by way of limitation), the in vitro diagnostic sensors of the presently disclosed inventive concept(s) may be potentiometric, amperometric, impedimetric, or conductometric sensors.

In certain embodiments, the in vitro diagnostic sensors of the presently disclosed inventive concept(s) may be biosensors. Non-limiting examples of target analytes detectable by biosensors of the presently disclosed inventive concept(s) include blood urea nitrogen (BUN), glucose, glutamate, lactate, ethanol, ascorbic acid, choline acetylcholine, creatinine, cholesterol, pyruvate, bilirubin, and the like. Any enzyme known in the art as capable of use in a biosensor for detection of a target analyte in a fluidic biological sample may be utilized as the enzyme of the sensor in accordance with the scope of the presently disclosed inventive concept(s). Non-limiting examples of enzymes useful in these biosensors include urease, glucose oxidase, glutamate oxidase, lactate oxidase, pyruvate oxidase, sarcosine oxidase, creatinine amidohydrolase, creatine amidinohydrolase, ascorbate oxidase, alcohol oxidase, cholesterol oxidase, choline oxidase, bilirubin oxidase, laccase, tyrosinase, alcohol dehydrogenase, glucose dehydrogenase, glutamate dehydrogenase, lactate dehydrogenase, pyruvate dehydrogenase, combinations thereof, and the like.

In another non-limiting embodiment of the presently disclosed inventive concept(s), the in vitro diagnostic sensor may be an ion selective electrode, and the substrate may therefore be an electrode. For example (but not by way of limitation), the in vitro diagnostic ion selective electrode may detect a target analyte selected from the group comprising magnesium, sodium, potassium, calcium, and chloride.

In certain embodiments of the presently disclosed inventive concept(s), the in vitro diagnostic sensor is intended for multiple uses over an extended period of time. In certain particular (but non-limiting) embodiments, the in vitro diagnostic sensor may be defined as a multi-use diagnostic sensor that has at least a 14 day use-life. For example (but not by way of limitation), the multi-use diagnostic sensor may substantially maintain the integrity thereof over a use-life of at least about 14 days (such as, but not limited to, at least about 30 days) and a sample capability of at least about 1000 samples (such as, but not limited to, at least about 2000 samples, or at least about 3000 samples).

Certain embodiments of the presently disclosed inventive concept(s) are also directed to a method of producing any of the in vitro diagnostic sensors described herein above or otherwise contemplated herein. In the method, a membrane comprising a modified polymer containing at least one surface adhesion functional group (as described in detail herein above) is disposed on a substrate. When the membrane is directly attached to the substrate, the at least one surface adhesion functional group attaches the membrane to the substrate. Alternatively, when the substrate has at least one suitable functional group disposed on at least a portion of a surface thereof, the surface adhesion functional group interacts with the at least one suitable functional group disposed on the surface of the substrate to attach the membrane to the substrate.

Certain embodiments of the presently disclosed inventive concept(s) are also directed to a method for detecting the presence and/or concentration of a target analyte in a fluidic biological sample. In the method, any of the in vitro diagnostic sensors described or otherwise contemplated herein is contacted with a biological sample, and the presence and/or concentration of target analyte present in the biological sample is measured using the diagnostic sensor. The presence and/or concentration of target analyte can be measured by any of the many and varied methods currently known in the art or otherwise contemplated herein (including, but not limited to, change in membrane potential or amperometry).

The in vitro diagnostic sensors of the presently disclosed inventive concept(s) may be provided in single assay/sensor form. Alternatively, the in vitro diagnostic sensors may be present as part of a single- or multi-use diagnostic sensor array assembly. Such assemblies will include a plurality of in vitro diagnostic sensors, wherein at least two of the plurality of in vitro diagnostic sensors are in vitro diagnostic sensors constructed in accordance with the presently disclosed inventive concept(s). In addition, the membranes of the at least two sensors are attached to the same substrate. In a particular (but non-limiting) embodiment, the diagnostic sensor array assembly includes at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least 25, at least 30, at least 35, at least 40, at least 45, at least 50, at least 55, at least 60, at least 65, at least 70, at least 75, at least 80, at least 85, at least 90, at least 95, at least 100, or more of the in vitro diagnostic sensors described or otherwise contemplated herein. In these embodiments, all of the membranes of the sensors may be disposed on the same substrate; alternatively, the diagnostic sensor array assembly may comprise multiple substrates.

Certain embodiments of the presently disclosed inventive concept(s) are also directed to methods of producing such diagnostic sensor array assemblies. In the method, a plurality of diagnostic sensors (each being constructed as described or otherwise contemplated herein) are formed on at least one surface of a substrate, and each of the plurality of diagnostic sensors are spatially positioned on the at least one surface of the substrate.

The diagnostic sensor array assemblies so constructed can be utilized in a method for detecting the presence and/or concentration of a plurality of target analytes in a fluidic biological sample. In the method, a fluidic biological sample is inserted into a blood gas, electrolyte, and/or metabolite instrument containing the diagnostic sensor array assembly, and the presence and/or concentration of each of the plurality of target analytes captured by the individual diagnostic sensors of the array assembly is measured and reported by the instrument. Therefore, the presently disclosed inventive concept(s) envisions simultaneously obtaining measurements for multiple analytes from multiple diagnostic sensors.

In each of the above detection methods, the fluidic biological sample may be selected from the group comprising whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

EXAMPLES

An Example is provided hereinbelow. However, the presently disclosed inventive concept(s) is to be understood to not be limited in its application to the specific experimentation, results, and laboratory procedures disclosed herein. Rather, the Examples are simply provided as one of various embodiments and are meant to be exemplary, not exhaustive.

As PVC is a major constituent of ISE membranes, a modification of the polymer backbone resulted in improved adhesion. This modified class of PVC polymer was decorated with a surface adhesion functional group, namely dopamine (3,4-dihydroxyphenethylamine), and then subsequently used to produce membranes for ISE's.

It has been shown that the catecholic amino acid DOPA is the primary functional group in Mussel foot proteins (Mfps) and is responsible for the adhesive capability of the mollusk mussel (Dalsin et al., and Forooshani et al.; incorporated supra); as disclosed therein, modified polymers containing DOPA have been synthesized for new adhesives or glues that exhibit strong adhesion to a range of surfaces even under long term exposure to aqueous environments.

Figure 2:
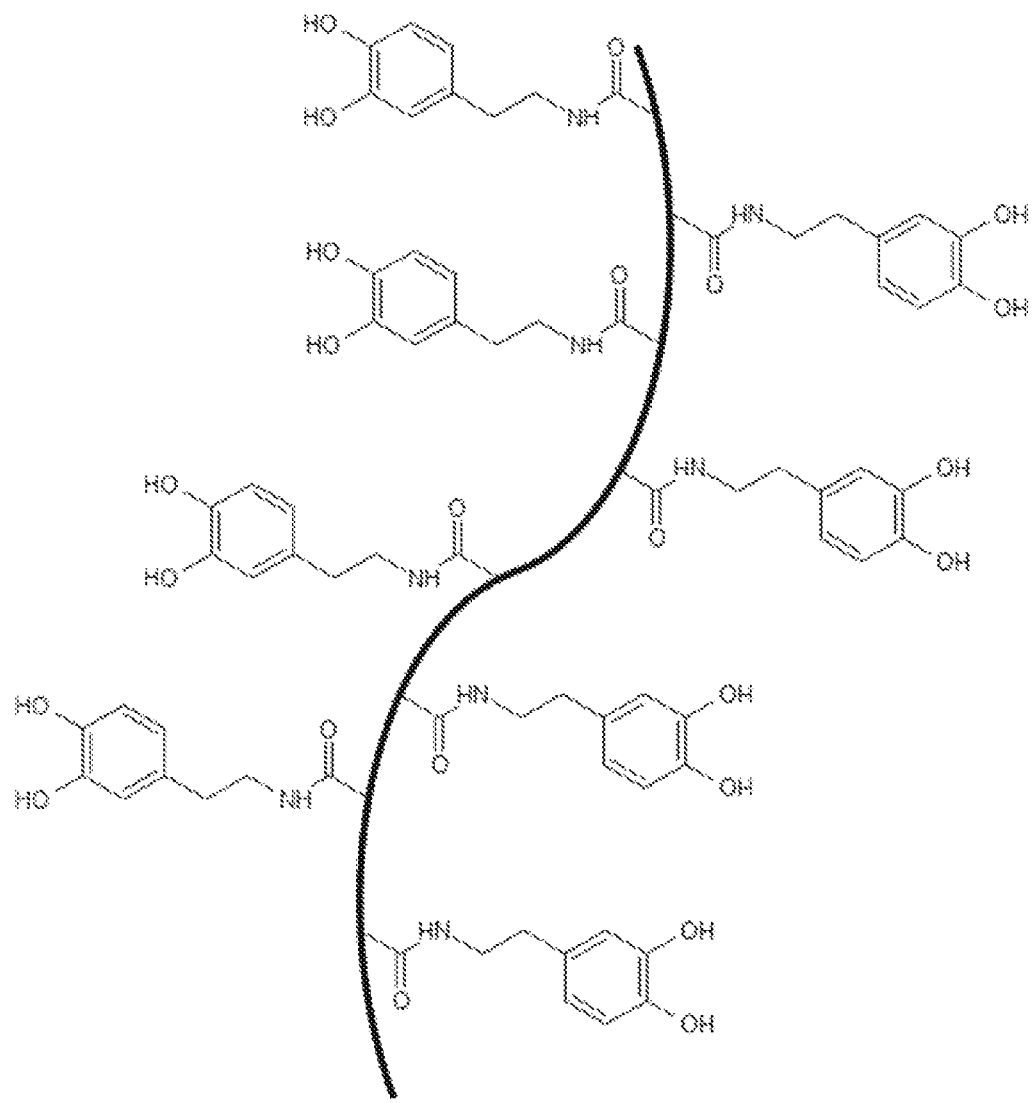
FIG. 2 graphically depicts a modified polymer comprising surface adhesion functional groups produced according to the method of FIG. 1.

As shown in FIG. 1, carboxylated-PVC was modified in one synthetic step using standard amide coupling techniques to yield a polymer that exhibits increased adhesion to metal, ceramic, and glass surfaces. All materials were readily available. The resulting modified polymer comprising carboxylated-PVC decorated with dopamine groups is shown in FIG. 2.

The resulting polymer can replace conventional PVC in ISE membranes and can be applied directly to native surfaces of ceramic, metal, or glass substrates using methods know in the art, such as (but not limited to) drop casting or spin coating. These membranes exhibit superior adhesion under aqueous conditions as compared to membranes with non-modified PVC.

Figure 3:
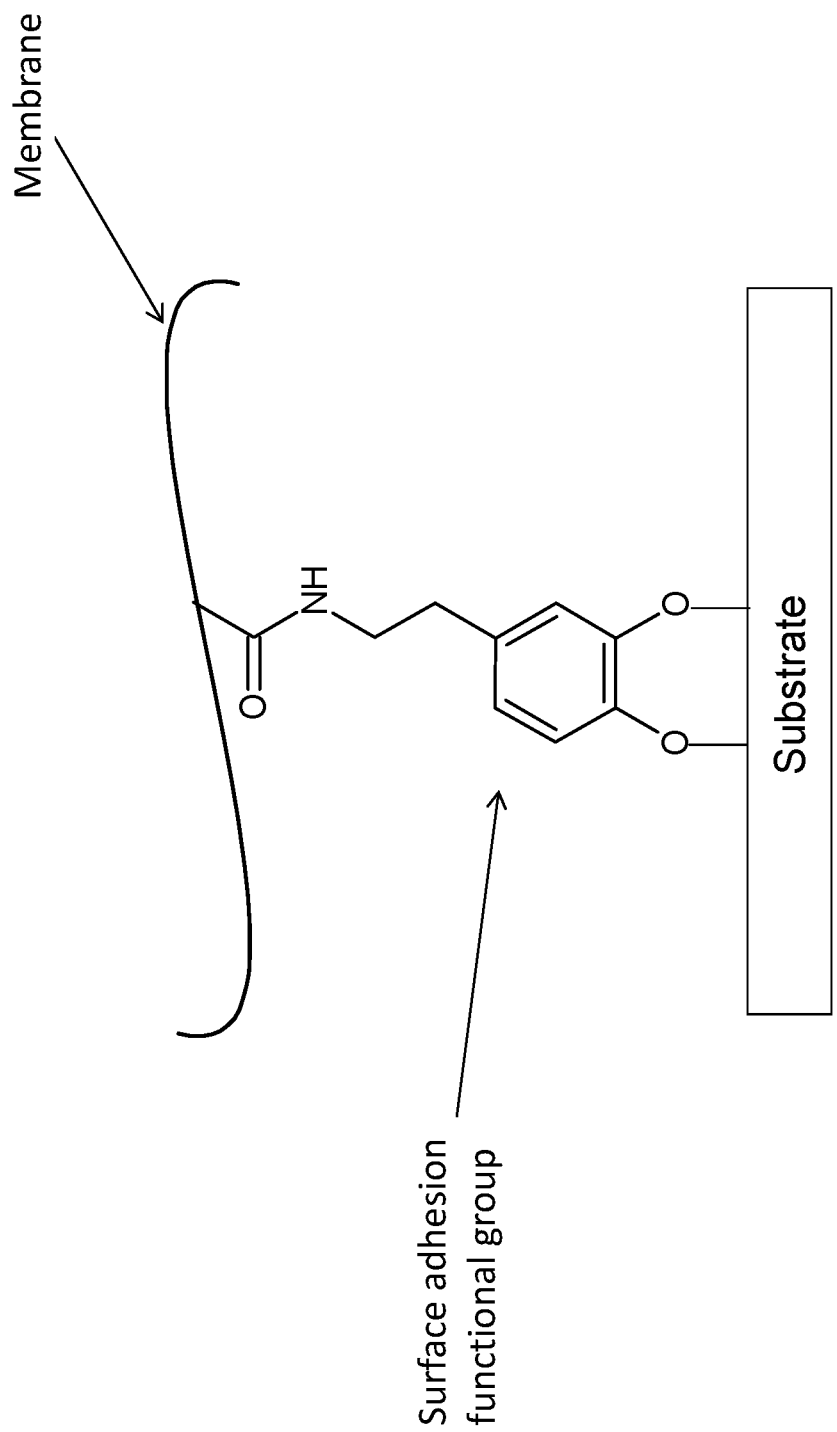
FIG. 3 graphically depicts attachment of a modified polymer-containing membrane to a substrate of an in vitro diagnostic sensor in accordance with one non-limiting embodiment of the presently disclosed inventive concept(s).

One embodiment of attachment of a membrane containing this modified polymer to a substrate is shown in FIG. 3. This embodiment relies on the strong adhesion properties of the catecholic functional group (1,2-dihydroxybenzene) to attach the modified polymer-containing membrane directly to the substrate (the specific bonding interaction shown is solely for purposes of illustration and is not to be construed as limiting).

Figure 4:
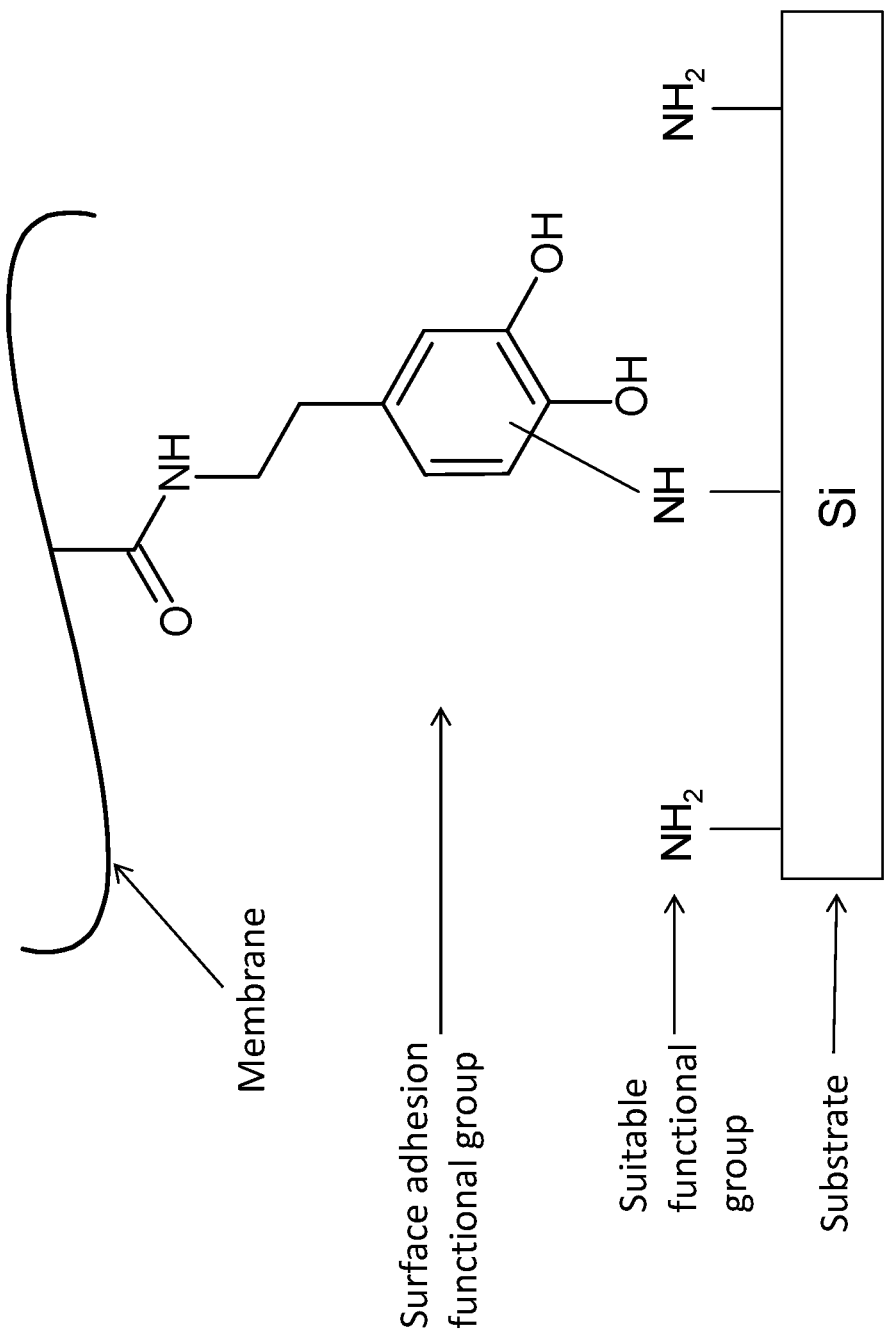
FIG. 4 graphically depicts attachment of a modified polymer-containing membrane to a substrate of an in vitro diagnostic sensor in accordance with a second non-limiting embodiment of the presently disclosed inventive concept(s).

Another embodiment of attachment of a modified polymer-containing membrane to a substrate is shown in FIG. 4. DOPA-containing compounds are also known to react with nucleophilic functional groups such as primary amines (Lee et al., incorporated supra). As shown in FIG. 4, a substrate (labeled Si) can be covered with a suitable functional group (labeled $NH_2$), and upon application of the modified PVC polymer to form the membrane, the surface adhesion functional group (i.e., DOPA) of the membrane interacts with the suitable functional group disposed on the surface of the substrate to further increase the adhesion of the membrane to the substrate. A suitable functional group for disposal on the surface of a ceramic or glass substrate is 3-Aminopropyl triethoxysilane.

Non-Limiting Embodiments of the Inventive Concept(s)

The following is a list of non-limiting illustrative embodiments of the inventive concepts disclosed herein:

1. An illustrative a membrane for an in vitro diagnostic sensor for detecting the presence and/or concentration of a target analyte in a fluidic biological sample, the membrane comprising: a polymer matrix comprising a polymer that has been modified to contain at least one surface adhesion functional group, wherein the at least one surface adhesion functional group enables attachment of the membrane to a substrate of the in vitro diagnostic sensor.

2. The illustrative membrane of embodiment 1, wherein the at least one surface adhesion functional group comprises a catecholic functional group (1,2-dihydroxybenzene).

3. The illustrative membrane of embodiment 1 or 2, wherein the polymer is polyvinyl chloride.

4. The illustrative membrane of embodiment 3, wherein the polyvinyl chloride is carboxylated-polyvinyl chloride or aminated-polyvinyl chloride.

5. The illustrative membrane of any one of embodiments 1-4, wherein the surface adhesion functional group comprises DOPA (3,4-dihydroxyphenylalanine) and/or dopamine (3,4-dihydroxyphenethylamine).

6. The illustrative membrane of any one of embodiments 1-5, wherein the surface adhesion functional group comprises from about 1 to about 99 weight percent of the membrane.

7. The illustrative membrane of embodiment 6, wherein the surface adhesion functional group comprises from about 2 to about 80 weight percent of the membrane.

8. The illustrative membrane of embodiment 7, wherein the surface adhesion functional group comprises from about 3 to about 60 weight percent of the membrane.

9. The illustrative membrane of any one of embodiments 1-8, further comprising a plasticizer.

10. The illustrative membrane of any one of embodiments 1-9, further defined as an ion-sensing membrane.

11. The illustrative membrane of embodiment 10, further defined as a magnesium, sodium, potassium, calcium, chloride, or pH sensing membrane.

12. The illustrative membrane of any one of embodiments 1-9, further defined as a membrane for a biosensor.

13. An illustrative in vitro diagnostic sensor for detecting the presence and/or concentration of a target analyte in a fluidic biological sample, the in vitro diagnostic sensor comprising: a substrate; and the membrane of any one of embodiments 1-12, wherein the surface adhesion functional group attaches the membrane to the substrate.

14. An illustrative in vitro diagnostic sensor for detecting the presence and/or concentration of a target analyte in a fluidic biological sample, comprising: a substrate having at least one suitable functional group disposed on at least a portion of a surface thereof; and the membrane of any one of embodiments 1-12, wherein the surface adhesion functional group interacts with the at least one suitable functional group disposed on the surface of the substrate to attach the membrane to the substrate.

15. The illustrative in vitro diagnostic sensor of embodiment 14, wherein the at least one suitable functional group disposed on at least a portion of the surface of the substrate comprises a nucleophilic functional group.

16. The illustrative in vitro diagnostic sensor of any one of embodiments 13-15, further defined as a potentiometric, amperometric, impedimetric, or conductometric sensor.

17. The illustrative in vitro diagnostic sensor of any one of embodiments 13-16, further defined as a biosensor.

18. The illustrative in vitro diagnostic sensor of embodiment 17, wherein the biosensor detects a target analyte selected from the group comprising blood urea nitrogen (BUN), glucose, glutamate, lactate, ethanol, ascorbic acid, choline acetylcholine, creatinine, cholesterol, pyruvate, and bilirubin.

19. The illustrative in vitro diagnostic sensor of embodiment 18, further defined as comprising an enzyme selected from the group comprising urease, glucose oxidase, glutamate oxidase, lactate oxidase, pyruvate oxidase, sarcosine oxidase, creatinine amidohydrolase, creatine amidinohydrolase, ascorbate oxidase, alcohol oxidase, cholesterol oxidase, choline oxidase, bilirubin oxidase, laccase, tyrosinase, alcohol dehydrogenase, glucose dehydrogenase, glutamate dehydrogenase, lactate dehydrogenase, and pyruvate dehydrogenase.

20. The illustrative in vitro diagnostic sensor of any one of embodiments 13-19, wherein the substrate is an electrode.

21. The illustrative in vitro diagnostic sensor of embodiment 20, further defined as an ion selective electrode.

22. The illustrative in vitro diagnostic sensor of embodiment 21, wherein the ion selective electrode detects a target analyte selected from the group comprising magnesium, sodium, potassium, calcium, and chloride.

23. The illustrative in vitro diagnostic sensor of any one of embodiments 13-22, further defined as a multi-use diagnostic sensor.

24. The illustrative in vitro diagnostic sensor of embodiment 23, further defined as having at least a 14 day use-life.

25. An illustrative method of producing the in vitro diagnostic sensor of any one of embodiments 13 and 16-24, the method comprising the step of: disposing a membrane on a substrate, the membrane comprising a polymer matrix comprising a polymer that has been modified to contain at least one surface adhesion functional group, and wherein the at least one surface adhesion functional group attaches the membrane to the substrate.

26. An illustrative method of producing the in vitro diagnostic sensor of any one of embodiments 14-24, the method comprising the step of: disposing a membrane on a substrate, the membrane comprising a polymer matrix comprising a polymer that has been modified to contain at least one surface adhesion functional group, wherein the substrate has at least one suitable functional group disposed on at least a portion of a surface thereof, and wherein the surface adhesion functional group interacts with the at least one suitable functional group disposed on the surface of the substrate to attach the membrane to the substrate.

27. An illustrative method for detecting the presence and/or concentration of a target analyte in a fluidic biological sample, the method comprising the steps of: contacting the in vitro diagnostic sensor of any one of embodiments 13-24 with a biological sample; and measuring the presence and/or concentration of the target analyte in the biological sample using the diagnostic sensor.

28. An illustrative diagnostic sensor array assembly, comprising: a plurality of in vitro diagnostic sensors, at least two of the plurality of in vitro diagnostic sensors being an in vitro diagnostic sensor of any one of embodiments 13-24, and wherein the membranes of at least two of the sensors is attached to the same substrate.

29. An illustrative method of producing a diagnostic sensor array assembly, the method comprising the step of: forming a plurality of diagnostic sensors on at least one surface of a substrate, wherein each of the plurality of diagnostic sensors are spatially positioned on the at least one surface of the substrate, and wherein at least one of the plurality of diagnostic sensors is formed by the method of embodiment 25 or 26.

30. An illustrative method for detecting the presence and/or concentration of a plurality of target analytes in a fluidic biological sample, the method comprising the steps of: (a) inserting a fluidic biological sample into a blood gas, electrolyte, and/or metabolite instrument containing the diagnostic sensor array assembly of embodiment 28; and (b) measuring the presence and/or concentration of each of the plurality of target analytes captured by the individual diagnostic sensors of the array assembly.

31. The illustrative method of embodiment 27 or 30, wherein the fluidic biological sample is selected from the group comprising blood, plasma, serum, urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

Thus, in accordance with the presently disclosed inventive concept(s), there have been provided compositions and devices, as well as methods of producing and using same, which fully satisfy the objectives and advantages set forth hereinabove. Although the presently disclosed inventive concept(s) has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed inventive concept(s).

What is claimed is:

1. A membrane for an in vitro diagnostic sensor for detecting the presence and/or concentration of a target analyte in a fluidic biological sample, the membrane comprising:

a polymer matrix comprising a polymer that has been modified to contain at least one surface adhesion functional group, wherein the at least one surface adhesion functional group enables attachment of the membrane to a substrate of the in vitro diagnostic sensor; and
a plasticizer.

2. The membrane of claim 1, wherein the polymer is polyvinyl chloride, carboxylated-polyvinyl chloride, and/or aminated-polyvinyl chloride.

3. The membrane of claim 1, wherein the at least one surface adhesion functional group comprises at least one of 1,2-dihydroxybenzene, DOPA (3,4-dihydroxyphenylalanine), and/or dopamine (3,4-dihydroxyphenethylamine).

4. An in vitro diagnostic sensor for detecting the presence and/or concentration of a target analyte in a fluidic biological sample, comprising:
a substrate having at least one suitable functional group disposed on at least a portion of a surface thereof; and
the membrane of claim 1, wherein the at least one surface adhesion functional group interacts with the at least one suitable functional group disposed on the surface of the substrate to attach the membrane to the substrate.

5. The in vitro diagnostic sensor of claim 4, wherein at least one of:
the polymer of the membrane is polyvinyl chloride, carboxylated-polyvinyl chloride, and/or aminated-polyvinyl chloride;
the at least one surface adhesion functional group of the membrane comprises at least one of 1,2-dihydroxybenzene, DOPA (3,4-dihydroxyphenylalanine), and/or dopamine (3,4-dihydroxyphenethylamine); and/or
the membrane is further defined as an ion-sensing membrane selected from the group consisting of a magnesium, sodium, potassium, calcium, chloride, or pH sensing membrane.

6. An in vitro diagnostic sensor for detecting the presence and/or concentration of a target analyte in a fluidic biological sample, comprising:
a substrate having at least one suitable functional group disposed on at least a portion of a surface thereof, wherein the at least one suitable functional group disposed on at least a portion of the surface of the substrate comprises a nucleophilic functional group; and
a membrane comprising a polymer matrix comprising a polymer that has been modified to contain at least one surface adhesion functional group; and
wherein the at least one surface adhesion functional group of the membrane interacts with the at least one suitable functional group disposed on the surface of the substrate to attach the membrane to the substrate.

7. The in vitro diagnostic sensor of claim 6, wherein at least one of:
the polymer of the membrane is polyvinyl chloride, carboxylated-polyvinyl chloride, and/or aminated-polyvinyl chloride; and/or
the at least one surface adhesion functional group of the membrane comprises at least one of 1,2-dihydroxybenzene, DOPA (3,4-dihydroxyphenylalanine), and/or dopamine (3,4-dihydroxyphenethylamine).

8. The in vitro diagnostic sensor of claim 7, further defined as a multi-use diagnostic sensor having at least a 14-day use-life.

9. The in vitro diagnostic sensor of claim 6, further defined as a potentiometric, amperometric, impedimetric, or conductometric sensor.

10. The in vitro diagnostic sensor of claim 6, wherein the substrate is an electrode.

11. The in vitro diagnostic sensor of claim 10, further defined as an ion selective electrode that detects a target analyte selected from the group comprising magnesium, sodium, potassium, calcium, and chloride.

12. An in vitro diagnostic biosensor for detecting the presence and/or concentration of a target analyte in a fluidic biological sample, wherein the target analyte is selected from the group comprising blood urea nitrogen (BUN), glucose, glutamate, lactate, ethanol, ascorbic acid, choline acetylcholine, creatinine, cholesterol, pyruvate, and bilirubin, the biosensor comprising:
a substrate having at least one suitable functional group disposed on at least a portion of a surface thereof; and
a membrane comprising a polymer matrix comprising a polymer that has been modified to contain at least one surface adhesion functional group; and
wherein the at least one surface adhesion functional group of the membrane interacts with the at least one suitable functional group disposed on the surface of the substrate to attach the membrane to the substrate.

13. The in vitro diagnostic sensor of claim 12, further defined as comprising an enzyme selected from the group comprising urease, glucose oxidase, glutamate oxidase, lactate oxidase, pyruvate oxidase, sarcosine oxidase, creatinine amidohydrolase, creatine amidinohydrolase, ascorbate oxidase, alcohol oxidase, cholesterol oxidase, choline oxidase, bilirubin oxidase, laccase, tyrosinase, alcohol dehydrogenase, glucose dehydrogenase, glutamate dehydrogenase, lactate dehydrogenase, and pyruvate dehydrogenase.

14. The in vitro diagnostic sensor of claim 12, wherein at least one of:
the polymer of the membrane is polyvinyl chloride, carboxylated-polyvinyl chloride, and/or aminated-polyvinyl chloride; and/or
the at least one surface adhesion functional group of the membrane comprises at least one of 1,2-dihydroxybenzene, DOPA (3,4-dihydroxyphenylalanine), and/or dopamine (3,4-dihydroxyphenethylamine).

15. A diagnostic sensor array assembly, comprising:
a plurality of in vitro diagnostic sensors, wherein each of at least two of the plurality of in vitro diagnostic sensors comprises a substrate and a membrane, wherein the substrate has at least one suitable functional group disposed on at least a portion of a surface thereof, and wherein the membrane comprises a polymer matrix comprising a polymer that has been modified to contain at least one surface adhesion functional group, wherein the at least one surface adhesion functional group of the membrane interacts with the at least one suitable functional group disposed on the surface of the substrate to attach the membrane to the substrate; and
wherein the membranes of at least two of the sensors is attached to the same substrate.

16. The diagnostic sensor array assembly of claim 15, wherein at least one of:
the polymer of the membrane of each of the at least two sensors is polyvinyl chloride, carboxylated-polyvinyl chloride, and/or aminated-polyvinyl chloride; and/or
the at least one surface adhesion functional group of the membrane of each of the at least two sensors comprises at least one of 1,2-dihydroxybenzene, DOPA (3,4-dihydroxyphenylalanine), and/or dopamine (3,4-dihydroxyphenethylamine).

17. The diagnostic sensor array assembly of claim 15, wherein at least one of:
   the membrane further comprises a plasticizer; and/or
   the at least one suitable functional group disposed on at least a portion of the surface of the substrate comprises a nucleophilic functional group.

18. A method for detecting the presence and/or concentration of a plurality of target analytes in a fluidic biological sample, the method comprising the steps of:
   (a) inserting a fluidic biological sample into a blood gas, electrolyte, and/or metabolite instrument containing the diagnostic sensor array assembly of claim 15; and
   (b) measuring the presence and/or concentration of each of the plurality of target analytes captured by the individual diagnostic sensors of the array assembly.

19. The method of claim 18, wherein the fluidic biological sample is selected from the group comprising blood, plasma, serum, urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

20. The method of claim 18, wherein at least one of:
   the polymer of the membrane of each of the at least two sensors is polyvinyl chloride, carboxylated-polyvinyl chloride, and/or aminated-polyvinyl chloride; and/or
   the at least one surface adhesion functional group of the membrane of each of the at least two sensors comprises at least one of 1,2-dihydroxybenzene, DOPA (3,4-dihydroxyphenylalanine), and/or dopamine (3,4-dihydroxyphenethylamine).

\* \* \* \* \*